United States Patent [19]
Tanuma

[11] Patent Number: 5,955,498
[45] Date of Patent: Sep. 21, 1999

[54] AGENT FOR PROPHYLAXIS AND THERAPY OF DISEASES

[76] Inventor: Sei-ichi Tanuma, 2-21-8-707, Bessho, Hachioji-shi, Tokyo 192-03, Japan

[21] Appl. No.: 08/765,298

[22] PCT Filed: Apr. 27, 1995

[86] PCT No.: PCT/JP95/00848

§ 371 Date: Dec. 23, 1996

§ 102(e) Date: Dec. 23, 1996

[87] PCT Pub. No.: WO95/28925

PCT Pub. Date: Nov. 2, 1995

[30]     Foreign Application Priority Data

Apr. 27, 1994  [JP]  Japan .................................. 6-090372
May 20, 1994   [JP]  Japan .................................. 6-107079

[51] Int. Cl.$^6$ .................... A61K 31/34; A61K 31/335
[52] U.S. Cl. ............................................ 514/474; 514/467
[58] Field of Search ................................. 514/467, 474

[56]            References Cited

U.S. PATENT DOCUMENTS 5,036,103  7/1991  Kochi ...................................... 514/467
5,130,145  7/1992  Oftebro et al. ........................ 514/467
5,135,948  8/1992  Borretzen et al. ..................... 514/467

FOREIGN PATENT DOCUMENTS

WO9535106 A1  12/1995  Japan ....................................... 514/467
WO9301817 A1   2/1993  United Kingdom .................... 514/467

OTHER PUBLICATIONS

"Benzylideneascorbate Induces Apoptosis in L929 Tumor Cells" by Tanuma et al, Biochemical and Biophysical Research Communications, vol. 194, No. 1, 1993 pp. 29–35.

"Effect of Sodium Benzylideneascorbate on Chemically–Induced Tumors in Rats" by Sakagami et al, Anticancer Research vol. 13, pp. 65–71 (1993).

Jariwalla et al., Nutr. Aids, 117–39, (Abstract only), 1994.

*Primary Examiner*—Jerome D. Goldberg
*Attorney, Agent, or Firm*—Sughrue, Mion, Zinn, Macpeak & Seas, PLLC

[57]            ABSTRACT

A pharmaceutical agent comprising an ascorbic acid, a derivative thereof or a salt thereof (ascorbic acids) as an active ingredient, for selectively inducing apoptosis of unnecessary or pathogenic cells to thereby prevent and/or treat diseases caused by said cells; a method for the prophylaxis and/or treatment of diseases caused by unnecessary or pathogenic cells, comprising selectively inducing apoptosis of said cells by the use of ascorbic acids; and use of ascorbic acids for the production of a pharmaceutical agent for selectively inducing apoptosis of unnecessary or pathogenic cells to thereby prevent and/or treat diseases caused by said cells. The ascorbic acids are low toxic and selectively induce apoptosis of unnecessary or pathogenic cells. Therefore, they are useful for the prophylaxis and/or treatment of the diseases caused by said cells. For example, they serve for use as anticancer agents and carcinostatic agents, as well as for the prophylaxis and/or treatment of many diseases caused by various viral infections. In particular, since they selectively induce apoptosis of unnecessary or pathogenic cells, they are useful for the prophylaxis and/or treatment of HIV viral infections and the prophylaxis and/or treatment of acquired immune deficiency syndrome (AIDS).

6 Claims, No Drawings

AGENT FOR PROPHYLAXIS AND THERAPY OF DISEASES

SPECIFICATION

1. Technical Field

The present invention relates to a pharmaceutical agent containing an ascorbic acid and the like as an active ingredient, which is for the prophylaxis and/or treatment of diseases caused by unnecessary or pathogenic cells, a method for the prophylaxis and/or treatment of said diseases, and to use of an ascorbic acid and the like for the production of a pharmaceutical agent for the prophylaxis and/or treatment of said diseases.

2. Background Art

With regard to the death of cells and tissues, apoptosis (active death of cells which is programmed in genes) has been drawing attention in recent years. Different from necrosis which is a pathological cell death, the apoptosis is considered to be the death incorporated from the first in the gene of the cell itself. That is, some external or internal factor triggers to activate the genes which program apoptosis, and apoptotic proteins biosynthesized by these genes or activation of existing apoptotic proteins cause active degeneration of the cells Per se, thus resulting in cell death.

DISCLOSURE OF TEH INVENTION

In view of the above situation, the present inventor has conducted intensive studies with the aim of developing a new pharmaceutical agent having an apoptosis inductive activity, and found that an ascorbic acid, a derivative thereof and a salt thereof (hereinafter also generally referred to as ascorbic acids) selectively induce apoptosis of unnecessary or pathogenic cells, and that they are useful for the prophylaxis and/or treatment of diseases caused by said cells, which resulted in the completion of the present invention.

Accordingly, the present invention provides the following.

1. A pharmaceutical agent containing an ascorbic acid, a derivative thereof or a salt thereof as an active ingredient, for selectively inducing apoptosis of unnecessary or pathogenic cells to thereby prevent and/or treat diseases caused by said cells.

2. A method for the prophylaxis and/or treatment of diseases caused by unnecessary or pathogenic cells, comprising selectively inducing apoptosis of said cells by the use of an ascorbic acid, a derivative thereof or a salt thereof.

3. Use of an ascorbic acid, a derivative thereof or a salt thereof for the production of a pharmaceutical agent for selectively inducing apoptosis of unnecessary or pathogenic cells to thereby prevent and/or treat diseases caused by said cells.

The ascorbic acid to be used in the present invention is a known compound. The derivative thereof is exemplified by benzylidene-ascorbic acid. The benzylidene-ascorbic acid is also a known compound which is specifically exemplified by 5,6-O-benzylidene-L-ascorbic acid of the following formula, and the like. The method of preparation thereof is described in Steroids, 12, p. 309 (1968) and others.

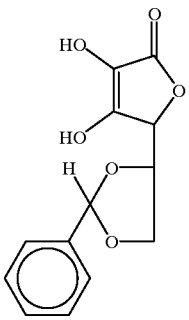

Other derivatives of ascorbic acid include, for example, an acylated compound of hydroxy at the 6-position of ascorbic acid [Japanese Patent Unexamined Publication No. 4103/1985 (WPI Ace NO: 85-046633/08), Expl. Cell Biol., 54, p. 245(86), Vitamin, 61, p. 199(87) etc.], ethylidene compound, undecylidene compound [Japanese Patent Unexamined Publication No. 131978/1983 (=U.S. Pat. No. 4,552,888, GB 2114571)], benzylidene compound [Japanese Patent Unexamined Publication No. 313476/1989 (WPI Acc NO: 90-034400/05)], and the like, wherein the 5-position hydroxy and 6-position hydroxy are combined.

Specific examples thereof include 6-propionylascorbic acid, 6-octanoylascorbic acid, 6-palmitoylascorbic acid, 6-benzoylascorbic acid, 5,6-O-(1-methylethylidene) ascorbic acid, 5,6-O-(1-benzyl-2-phenylethylidene)ascorbic acid, 5,6-O-undecylidene-ascorbic acid, 5,6-O-p-nitrobenzylidene-ascorbic acid and the like. These derivatives can be prepared by the methods disclosed in the above-mentioned references.

Examples of the salts of ascorbic acid and derivatives thereof include pharmaceutically acceptable salts such as alkali metal salts (e.g., lithium, sodium and potassium); alkaline earth metal salts (e.g., calcium, magnesium and berillium); aluminum salts; organic salts (e.g., triethylamine and pyridine); and the like. These salts can be prepared by the methods disclosed in Japanese Patent Unexamined Publication No. 139619/1985 (=U.S. Pat. No. 5,036,103, EP 148094) and the like.

Inasmuch as the ascorbic acids to be used for the agent for the prophylaxis and therapy of diseases of the present invention are low toxic and selectively induce apoptosis of unnecessary or pathogenic cells, they are useful for the prophylaxis and/or treatment of the diseases caused by said cells. Specifically, they are useful as an anticancer drug and carcinostatic agent, as well as for the prophylaxis and/or treatment of many diseases caused by various viral infections. Particularly, since they selectively induce apoptosis of unnecessary or pathogenic cells, they are useful for the prophylaxis and/or treatment of HIV infections, and further for the prophylaxis and/or treatment of acquired immune deficiency syndrome (AIDS).

The agent for the prophylaxis and therapy of diseases of the present invention is provided as solid preparations, semi-solid preparations or liquid preparations in admixture with organic or inorganic carriers and/or excipients suitable for external, oral or local administration. The agent for the prophylaxis and therapy of diseases of the present invention is used to provide a suitable dosage form such as powders, granules, tablets, pellets, capsules, suppositories, solutions, emulsions, suspensions, injections, syrups, external agents and the like, together with pharmacologically acceptable auxiliary ingredients.

Examples of such auxiliary ingredients include those effectively used for the production of solid, semi-solid or liquid preparations, such as water, glucose, lactose, gelatin, mannitol, starch paste, magnesium trisilicate, corn starch, keratin, colloidal silica, potato starch, urea and the like. Moreover, auxiliaries such as stabilizers, extenders, colorants and aromatic agents are also encompassed. For a retained activity of the ascorbic acids, a preservative may be added. The agent should contain a sufficient amount of the ascorbic acids to bring the desired therapeutic effects on the progress or symptom of the related diseases.

When the inventive agent for prophylaxis and therapy of diseases is administered to human, an effective amount of the ascorbic acids is preferably administered parenterally by, for example, injection, or orally administered. While the dose of the inventive agent for prophylaxis and therapy of diseases varies depending on sex, age, body weight, symptom, therapeutic effects, administration route, administration period and the like, it is typically about 100–3,000 mg/day to an adult patient.

The present invention is described in more detail by referring to Experimental Examples and Formulation Examples, which are not to be construed as limiting the invention.

EXPERIMENTAL EXAMPLE 1

In an HIV expression system using cells (hereinafter to be referred to as U1 cells) wherein two copies of the HIV-1 gene (HTLV-III B strain) had been introduced into U937 cells (human monoblastoid cells), the induction of apoptosis of HIV-expressing cells by sodium salt of 5,6-O-benzylidene-L-ascorbic acid (hereinafter to be referred to as SBA) was confirmed. Note that said U1 cells do not express HIV in the absence of an inducer such as TPA (phorbol ester) or TNF (tumor necrosis factor). That is, latent infection with HIV. When the above-said inducer is reacted with the cells in this state, about 30% of the cells have been confirmed to become HIV-expressing cells which express HIV.

For confirmation of the state of the cells when replication of HIV is suppressed by SBA, the viability was examined by a dye-exclusion test using trypan blue.

The results are shown in the following Table 1.

TABLE 1

| SBA concentration | Viability of cell (%) | |
|---|---|---|
| ($\mu$g/ml) | No addition of TPA | Addition of TPA 1 ng/ml |
| 0 | 100 | 83 |
| 25 | 100 | 77 |
| 50 | 100 | 66 |
| 100 | 99 | 58 |
| 200 | 99 | 49 |
| 400 | 95 | 47 |
| 800 | 87 | 38 |

It is considered that the cells (HIV positive cells) in which HIV had been relpicated by TPA were killed by SBA. To confirm whether or not said cell death was apoptosis, the morphological alterations of the cells which are characteristic of apoptosis were examined by an electron microscope and the presence or otherwise of DNA fragmentation was examined by agarose gel electrophoresis. As a result, the addition of SBA was found to have led to cell shrinkage, nuclear condensation and disapearance of cell surface microvilli. When SBA (100 $\mu$g/ml) was used in the absence of TPA, fragmentation of DNA was not observed (namely, apoptosis was not induced), but when SBA (100 $\mu$g/ml) was used in the presence of TPA (1 ng/ml), fragmentation of DNA was observed. That is, SBA selectively induced apoptosis of the cells replicating HIV to cause death of the cells.

EXPERIMENTAL EXAMPLE 2

(toxicity)

An Sba Solution (10 mg/ml) was administered to mice. As a result, an intrevenous administration of 1,000 mg/kg body weight did not cause death of the mice.

EXPERIMENTAL EXAMPLE 3

Induction of apoptosis by SBA was confirmed in human promyelocytic leukemia (HL -60). As a control, normal human lymphocytes (lympho) were used.

Fragmentation of DNA was examined according to Experimental Example 1, based on which the proportion of the cells in which apoptosis was induced after 6 hours' treatment of respective cells in the presence of SBA was calculated. The results are shown in the following Table 2.

TABLE 2

| SBA concentration | Proportion (%) of cells with apoptosis induction | |
|---|---|---|
| (mM) | HL-60 | Normal human lymphocyte |
| 0 | 0 | 0 |
| 0.03 | 2 | 0 |
| 0.1 | 1 | 0 |
| 0.3 | 42 | 0 |
| 1 | 65 | 0 |
| 3 | 74 | 0 |
| 10 | 90 | 1 |
| 30 | — | 3 |

SBA concentration-dependently induced apoptosis of HL-60 tumor cells. However, it did not induce apoptosis in normal human lymphocytes at the same concentration, which confirms that the apoptosis induction of SBA was based on the selectivity for tumor cells. SBA did not affect normal human lymphocytes up to the concentration of 30 mM, thus showing sufficiently low cytotoxicity.

EXPERIMENTAL EXAMPLE 4

In the same manner as in Experimental Example 3 except that ascorbic acids were used instead of SBA, the tests were run. The results are shown in the following Table 3.

TABLE 3

| Ascorbic acid concentration | Proportion (%) of cells with apoptosis induction | |
|---|---|---|
| (mM) | HL-60 | Normal human lymphocyte |
| 0 | 0 | 0 |
| 0.03 | 2 | 0 |
| 0.1 | 1 | 0 |
| 0.3 | 42 | 0 |
| 1 | 82 | 0 |
| 3 | 86 | 1 |
| 10 | — | 2 |

The ascorbic acid concentration-dependently induced apoptosis of HL-60 tumor cells. However, it did not induce apoptosis of normal human lymphocytes at the same concentration, which confirms that the apoptosis induction of ascorbic acid was based on the selectivity for tumor cells. The ascorbic acid did not affect normal human lymphocytes up to the concentration of 10 mM, thus showing sufficiently low cytotoxicity.

FORMULATION EXAMPLE 1

Tablet

| | | |
|---|---|---|
| (1) | SBA | 50 g |
| (2) | Microgranule No. 209 for direct compression | |
| | (manufactured by Fuji Kagaku) | 70 g |
| | Magnesium aluminum metasilicate | 20% |
| | Corn starch | 30% |
| | Lactose | 50% |
| (3) | Crystalline cellulose | 60 g |
| (4) | CMC calcium | 18 g |
| (5) | Magnesium stearate | 2 g |

(1) to (4) were uniformly mixed. Then, (5) was added, mixed and the mixture was compressed into tablets weighing 200 mg per tablet. The tablets may be applied as necessary with an enteric film coating conventionally used, such as polyvinyl acetaldiethylaminoacetate or food dye.

FORMULATION EXAMPLE 2

Capsule

| | | |
|---|---|---|
| (1) | SBA | 1000 g |
| (2) | Lactose | 960 g |
| (3) | Magnesium stearate | 40 g |

The above ingredients were uniformly mixed and the mixture was packed in hard gelatin capsules by 200 mg each.

FORMULATION EXAMPLE 3

Injection

| | | |
|---|---|---|
| (1) | SBA | 100 mg |
| (2) | Glucose | 100 mg |
| (3) | Physiological saline | 10 ml in total |

(1) and (2) were dissolved in (3), and the solution was filtered through a membrane filter, which was followed by filtration again for sterilization. The filtrate was aseptically dispensed into vials. A nitrogen gas was filled and the vials were sealed to give intravenous injections.

FORMULATION EXAMPLES 4–6

In the same manner as in Formulation Examples 1–3 except that ascorbic acids are used instead of SBA, respective preparations are prepared.

INDUSTRIAL APPLICABLITY

The ascorbic acids to be contained in the agent for the prophylaxis and/or treatment of diseases of the present invention are low toxic and selectively induce apoptosis of unnecessary or pathogenic cells. Therefore, they are useful for the prophylaxis and/or treatment of the diseases caused by said cells. For example, they serve for use as anticancer agents and carcinostatic agents, as well as for the prophylaxis and/or treatment of many diseases caused by various viral infections. In particular, since they selectively induce apoptosis of unnecessary or pathogenic cells, they are useful for the prophylaxis and/or treatment of HIV infections and the prophylaxis and/or treatment of acquired immune deficiency syndrome (AIDS).

What is claimed is:

1. A method for the prophylaxis and/or treatment of diseases caused by cells infected with a virus, comprising selectively inducing apoptosis of said cells by administering to a subject in need thereof a therapeutically effective amount of a compound selected from the group consisting of 6-O-acyl-ascorbic acid, 5,6-O-ethylidene-ascorbic acid, 5,6-O-undecylidene-ascorbic acid, 5, 6-O-benzylidene-ascorbic acid and salt thereof for selectively inducing apoptosis of said cells.

2. The method of claim 1, wherein said compound is 5,6-O-benzylidene-ascorbic acid or salt thereof.

3. The method of claim 1, wherein said virus is HIV.

4. The method of claim 1, wherein said subject is a human.

5. The method of claim 1, wherein said compound is selected from the group consisting of 6-propionylascorbic acid, 6-octanoylascorbic acid, 6-palmitoylascorbic acid, 6-benzoylascorbic acid, 5,6-O-(1-methylethylidene) ascorbic acid, 5,6-O-(1-benzyl-2-phenylethylidene)ascorbic acid, 5,6-O-undecylidene-ascorbic acid, 5,6-O-p-nitrobenzylidene-ascorbic acid and salt thereof.

6. The method of claim 1 wherein said compound is sodium 5,6-O-benzylidene-L-ascorbate.

* * * * *